Figure 1:
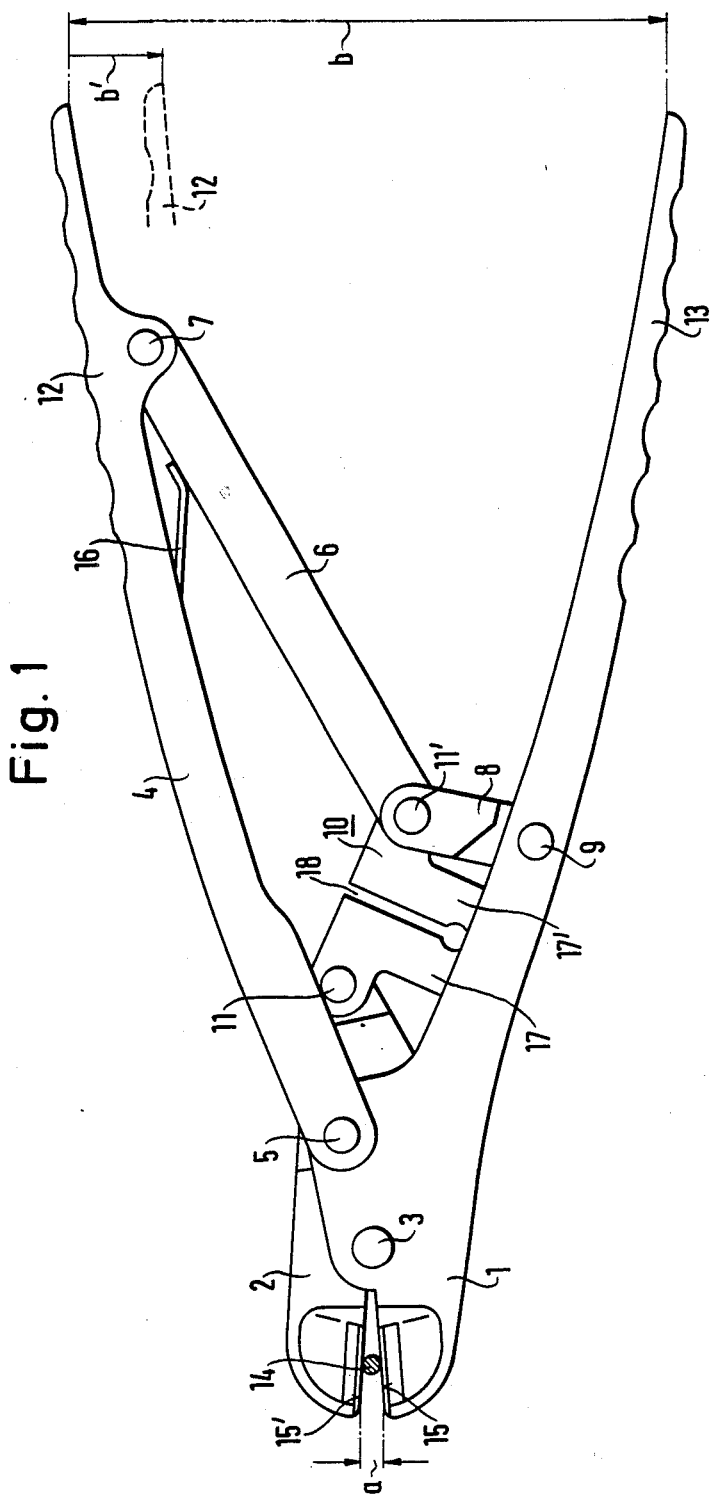

United States Patent
Mäntele

[19]
[11] Patent Number: 4,891,883
[45] Date of Patent: Jan. 9, 1990

[54] PLIERS

[75] Inventor: Erwin Mäntele, Tuttlingen, Fed. Rep. of Germany

[73] Assignee: Delma elektro- und medizinische Apparatebau GmbH, Tuttlingen, Fed. Rep. of Germany

[21] Appl. No.: 287,185

[22] Filed: Dec. 20, 1988

[30] Foreign Application Priority Data

Dec. 22, 1987 [DE] Fed. Rep. of Germany ....... 3743605

[51] Int. Cl.$^4$ .......................................... B26B 17/00
[52] U.S. Cl. ...................................... 30/190; 30/251
[58] Field of Search ............................... 30/186–193, 30/249–251

[56] References Cited

U.S. PATENT DOCUMENTS

| | | | |
|---|---|---|---|
| 1,046,771 | 12/1912 | Goodnow | 30/190 X |
| 1,354,843 | 10/1920 | Province | 30/188 |
| 3,170,345 | 2/1965 | Poingt | 30/190 X |

FOREIGN PATENT DOCUMENTS 2633 of 1893 United Kingdom .................. 30/190

Primary Examiner—Frank T. Yost
Assistant Examiner—Willmon Fridie
Attorney, Agent, or Firm—Townsend and Townsend

[57] ABSTRACT

The invention relates to a pair of surgical pliers for the cutting through of wires (14), screws or the like comprising a cutter gripping lever (1) having a cutting edge (15) at its front end and a handle (13) at its rear end, and a cutting lever (2) pivotally connected to the cutter gripping lever by means of a cutting lever hinge (3) with the cutting lever having a second cutting edge (15') disposed opposite to the first cutting edge (15). A gripping lever (4) is also pivotally connected to the cutter gripping lever (1). A transmission is arranged between the gripping lever (4) and the cutting lever (2). The input drive member (6) of the transmission braced against the cutter gripping lever (1) is loaded by the gripping lever whereas the output drive member (11) of the transmission acts on the cutting lever (2) at the side remote from the cutting edge (15) of the cutting lever hinge (3) which connects the cutting lever (2) to the cutter gripping lever (1). In this way the same relative pivotal movements of the gripping lever (4) relative to the cutter gripping lever (1) bring about a pivotal movement of the cutter lever (2) relative to the cutting gripping lever (1) which becomes smaller as the distance b between the gripping lever (4) and the cutter gripping lever (1) becomes smaller, so that the mechanical advantage automatically increases as this distance b becomes smaller.

11 Claims, 6 Drawing Sheets

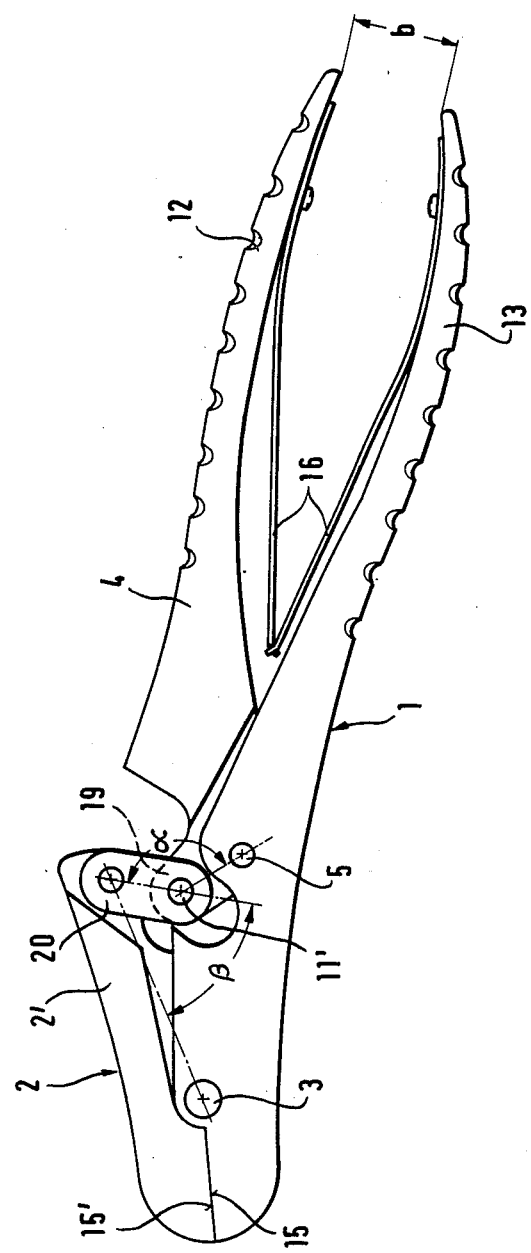

PLIERS

The invention relates to a pair of pliers, in particular for surgical purposes for the cutting through of wires, screws or the like, comprising a cutter gripping lever having a cutting edge at its front end and a handle at its rear end, wherein a cutting lever having a second cutting edge disposed opposite to the first cutting edge is pivotally connected to the cutter gripping lever by means of a cutting lever hinge, wherein a gripping lever is pivotally connected to the cutter gripping lever behind the cutting lever hinge by means of a gripping lever hinge, and wherein a transmission is arranged between the gripping lever and the cutting lever.

In surgical operations on bones the need frequently exists to shorten steel wires of high ductility. Thus for example, Kirschner wires with diameters of 1 to 3 mm are so bored through joints for wire traction that they project on both sides. The same wires are used as guide skewers for guidance when inserting hollow screws. Moreover whole finger members are bored through in the longitudinal direction with Kirschner wires for reliable fixations in the surgery of the hand. These Kirschner wires come in commercially available lengths and are adapted to the prevailing circumstances and shortened during surgical operations.

Furthermore it is usual, when using a so-called fixator to drive external Steinmann pins through the bones of extremities. These Steinmann pins must then likewise be externally shortened to the correct length for the installation on the fixator. The same applies for Schanz screws.

In all these cases pliers of the initially named kind are used for material separation since the sawing off or grinding through of the named wires or screws is prohibited for reasons of hygiene. The material separation must therefore take place chiplessly since sawing swarf or grinding dust must not be allowed to enter into the open wound because of the risk of infection.

The pliers which have previously been used in surgery mainly have the form of a side cutter, or more rarely have the form of a bolt cutter with end face cutting edges, and have a transmission between the gripping levers in order to make it possible for the operator to exert the necessary force from the cutting edges onto the bar, wire or screw.

As the angle of opening of the handles of the pliers is restricted through the nature of the human hand, and by the diameter of the wires or screws to be cut, natural limits are placed on the mechanical advantage available through the transmission. As a result the operator is frequently forced to use both hands, in particular for cutting through wires or screws of larger diameter, in order to obtain the required cutting force in this way. This is however relatively complicated and involved.

The invention is now based on the object of providing a pair of surgical pliers of the initially named kind which makes it possible to cut through even wires screws of larger diameter simply and with a reasonable expenditure of force in one-handed operation.

The invention is solved in accordance with the invention by a pair of pliers of the initially named kind which is characterised in that the input drive member of the transmission is loaded by the gripping lever; and in that the output drive member of the transmission acts on the cutting lever at the side remote from the cutting edge of the cutting lever hinge which supports the cutting lever on the cutter gripper lever, with like relative pivotal movements of the gripping lever relative to the cutter gripping lever bringing about progressively smaller pivotal movements of the cutting lever relative to the cutter gripping lever as the distance between the cutting lever and the cutter gripping lever becomes smaller, so that the mechanical advantage increases automatically as the distance becomes smaller.

As a result of these measures provided in accordance with the invention one ensures that for the same force acting on the handles of the pliers the separating force exerted by the cutting edges of the pliers on the wire increases during the progressive cutting process. Thus the operator is not forced to use a second hand for the cutting operation when cutting through wires or screws during an operation. In this way, the use of the pliers is made substantially simpler and the operator has the other hand free for further activities.

The operator can first move the pliers until the workpiece becomes clamped with a small mechanical advantage. During this the cutting edges move through a relatively large path relative to one another in relation to a specific closing path of the handgrips. At the start of the cutting process, when the force required at the cutting edges is still low, the mechanical advantage changes little so that the cutting edges can always move through a relatively large path. Only during the cutting operation does the mechanical advantage, and thus also the force at the cutting edges, increase rapidly in accordance with the invention, while the path through which the cutting edges move in relation to the closing path of the handgrips reduces greatly.

It is an advantage with this arrangement that the cutting edges can easily be opened in order to grasp a workpiece without having to pivot the handgrips excessively far away from one another, since the path conversion ratio is still relatively large when the pliers are opened.

A further embodiment of the invention is characterised in that the mechanical advantage increases substantially quadratically as the distance between the gripping lever and the cutter gripping lever becomes smaller. In this way it is ensured, with the force acting on the plier handles again remaining constant, that the force exerted by the cutting edges on the article to be cut through, which is in particular a round article, is so increased that the cutting pressure of the cutting edges on the article which is required for cutting of the material remains substantially constant throughout the entire cutting process. In this respect the increase of the mechanical advantage provided by the invention is necessary because the contact surface of the cutting edges likewise increases substantially quadratically on penetration into the article. The invention thus ensures, in addition to reliable cutting through of the wires or screws, a very uniform application of force, so that the surgeon can operate the pliers of the invention during the operation purposefully and extremely uniformly. Thus the surgeon does not have to exert excessive pressure to cut through a wire or screw. Moreover, the use of the pliers substantially minimizes jolts at the end of the cutting process when the two cutting edges finally cut through the wire or screw.

In a preferred embodiment of the invention provision is made for a toggle lever drive to be used as a transmission, with the input drive member being formed by a transmission lever pivotally connected at its first end on the gripping lever, with the transmission lever and the gripping lever forming a first toggle lever, and with the other end of the transmission lever loading a toggle lever joint of a second toggle lever, which consists of a support lever which is pivotally connected to the cutter gripping lever, and of an intermediate lever which extends from the toggle lever joint to the cutting lever at which it is pivotally connected at an intermediate hinge. In this way one provides a pair of pliers which is easy to use, which is of simple design and construction and which can thus be manufactured at favourable cost.

In an advantageous further development of the invention provision is made that an acute angle which becomes smaller on actuating the pliers is provided between the gripping lever and the transmission lever and that an obtuse angle which becomes larger on actuating the pliers is provided between the support lever and the intermediate lever, wherein, when the cutting edges are closed, the transmission lever lies approximately parallel to the gripping lever and the second toggle lever lies shortly before its extended position. Through this special choice of the angle of the two toggle levers it is possible to ensure that the mechanical advantage is particularly large in the end region of the closing movement of the pliers since relatively large changes in angle of the toggle levers only bring about a very small displacement of their hinge points.

In order to be able to match the mechanical advantage that is required of the pliers of the invention to the prevailing circumstances in a simple manner provision is made, in accordance with a further embodiment of the invention that the transmission lever which is pivotally connected to the gripping lever is approximately 3 to 6 times and preferably 4 to 5 times and in particular 4.5 times longer than the support lever, with the spacing between the first hinge which connects the gripping lever with the cutter gripping lever and the second hinge which forms the toggle hinge of the first toggle lever is approximately 1.5 to 3 times and preferably 2 to 2.5 times larger than the distance between the first hinge and the support hinge which holds the support lever on the cutter gripping lever.

In order to obtain a particularly compact and easy to handle construction of the pliers which is important for its use during an operation, another embodiment of the invention provides that the length of the intermediate lever amounts to between 1/6 to ⅔, preferably between ¼ to ½ and in particular ⅓ of the length of the transmission lever.

In a further preferred embodiment of the invention provision is made that the length of the intermediate lever can be made smaller, with the intermediate lever being constructed as a spring. In this way it is possible to ensure that on closing the pliers to cut through wires or screws of large diameter the closing angle between the cutting edges initially remains unchanged after cutting to a small degree into or clamping the wire or screw by means of the cutting edges whereas the closing angle of the handles of the pliers, i.e. the spacing between the cutter gripping lever and the gripping lever, becomes smaller until the mechanical advantage for the force exerted by the cutting edges has increased to a level such that the pressure exerted by the cutting edges of the pliers corresponds to a cutting pressure, so that the process of cutting the wire or screw clamped between the cutting edges of the pliers can be continued. Thus the operator only needs to use the same force when cutting through thicker wires or screws as is required for cutting through thinner wires. Thus one obtains a particularly uniform actuation of the pliers of the invention which is independent of the thickness of the article to be cut through.

In order to be able to cut through articles of particularly high notch impact strength a further embodiment of the invention provides that the intermediate lever is formed by a U-shaped compression spring, the spring slot of which restricts the change of length of the intermediate lever, with the maximum reduction in length of the intermediate lever amounting to approximately 1/10 to ½, preferably 1/7 to ¼ and in particular to 1/5 of the total displacement path of the toggle hinge. In this way one ensures that the cutting edges of the pliers fully contact one another when the handles of the pliers are fully pressed together. Thus troublefree cutting through of workpieces during the operation is always ensured.

In another embodiment of the invention provision is made that the second hinge which forms the toggle hinge of the first toggle lever and/or the support hinge is/are adjustably arranged in the direction of the gripping lever or of the cutter gripping lever respectively, on the same. In this way a further possibility is provided for reducing the closing angle of the pliers' handles, on cutting through wires or screws of larger diameter after only cutting fractionally into the workpiece or on clamping onto workpiece, to such a degree that the mechanical advantage increases so far that the cutting edges can then exert the separating force which is required on the workpiece.

A particular simple embodiment which operates with only one toggle lever arrangement is characterised, in accordance with the invention, in that the gripping lever is extended on the far side of the gripping lever hinge by a relatively short toggle lever arm which, via a toggle lever hinge, acts on a toggle lever link which together with the toggle lever arm forms a toggle lever and which is pivotally connected at the end remote from the toggle lever joint to the lever arm of the cutting lever remote from the cutting edge with respect to the cutting lever hinge, with the toggle lever passing on reduction of the spacing between the gripping lever and the handle from a greatly kinked position into a more extended position, and with the toggle lever link including a substantial angle of preferably at least 30° to 40°, in particular 35° with the said lever arm in the opened state of the pliers, with this angle expediently progressively approaching 90° as the cutting edges move together and/or preferably amounting to 40° to 80°, expediently to 60° to 70° and in particular to approximately 60°, when the cutting edges are closed or are approximately closed.

Here provision is in particular made that the toggle lever has a kink angle $\alpha$ of the order of magnitude of 90° and preferably somewhat less than 90°, in particular approximately 80° to 90°, in the non-actuated state of the pliers and, in the fully compressed state of the pliers is located close to its extended state and preferably has a kink angle $\alpha$ between 120° and 150°, preferably 130° to 140°.

Furthermore it is expedient when the lever arm between the cutting lever hinge and the toggle lever link is longer by a factor of 1.5 to 2 than the lever arm carrying the cutting edge.

Figure 2:
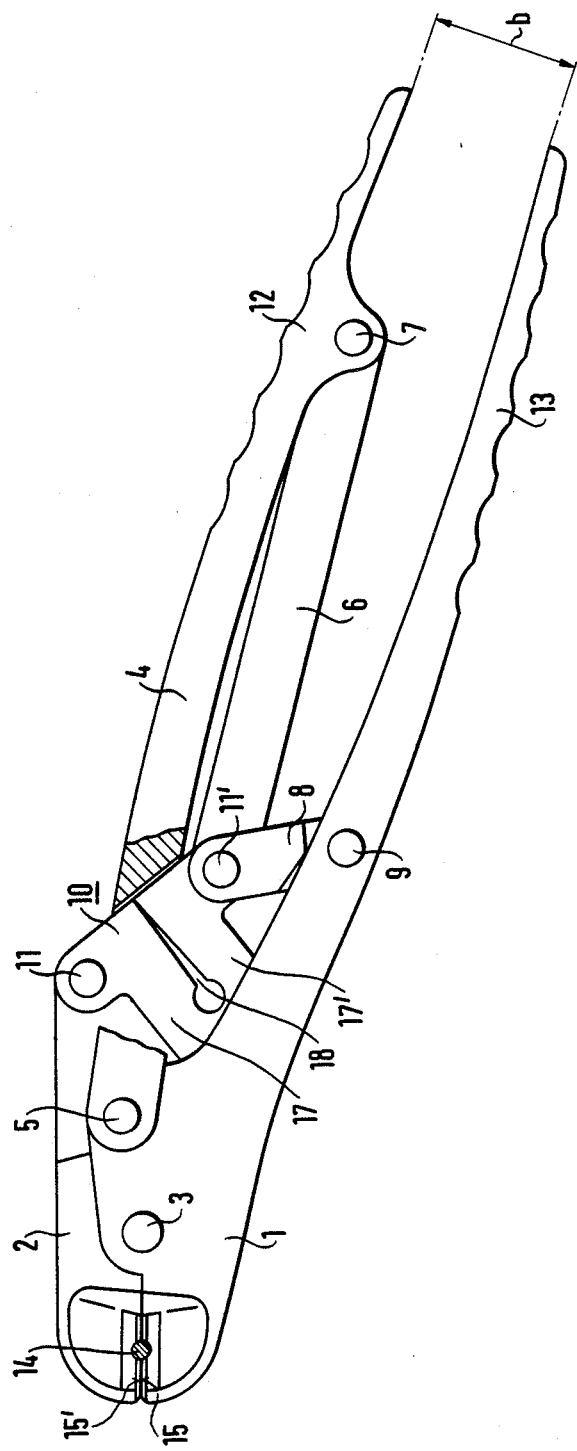
Figure 3:
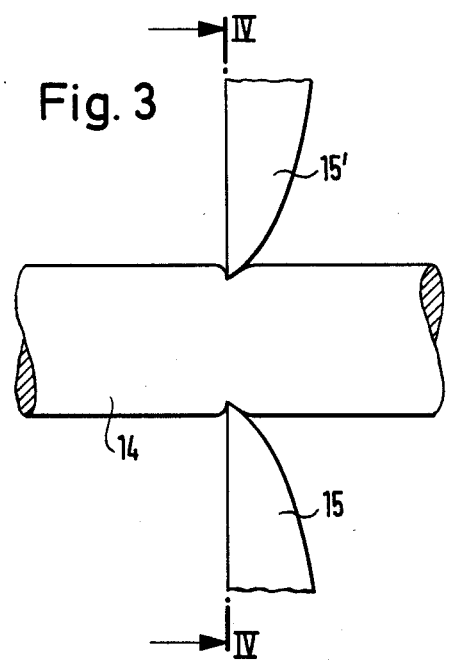
Figure 4:
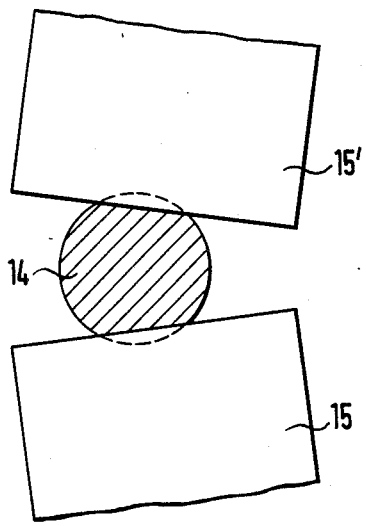
Figure 5:
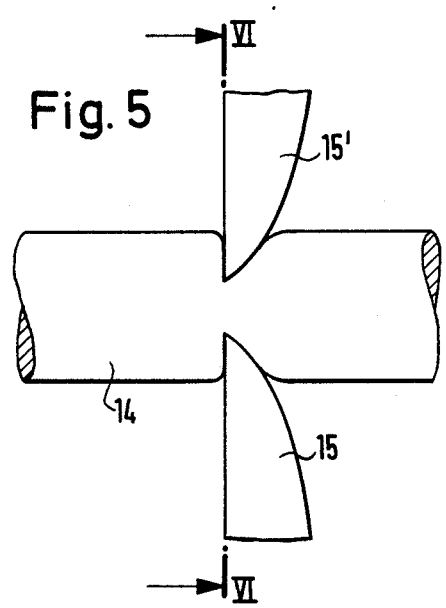
Figure 6:
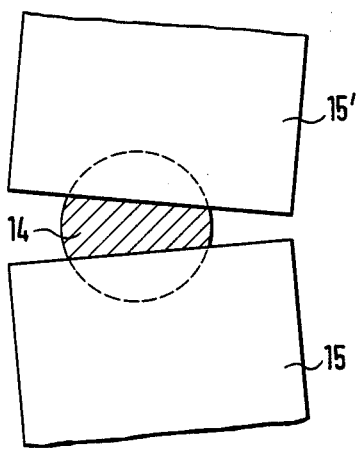
Figure 7:
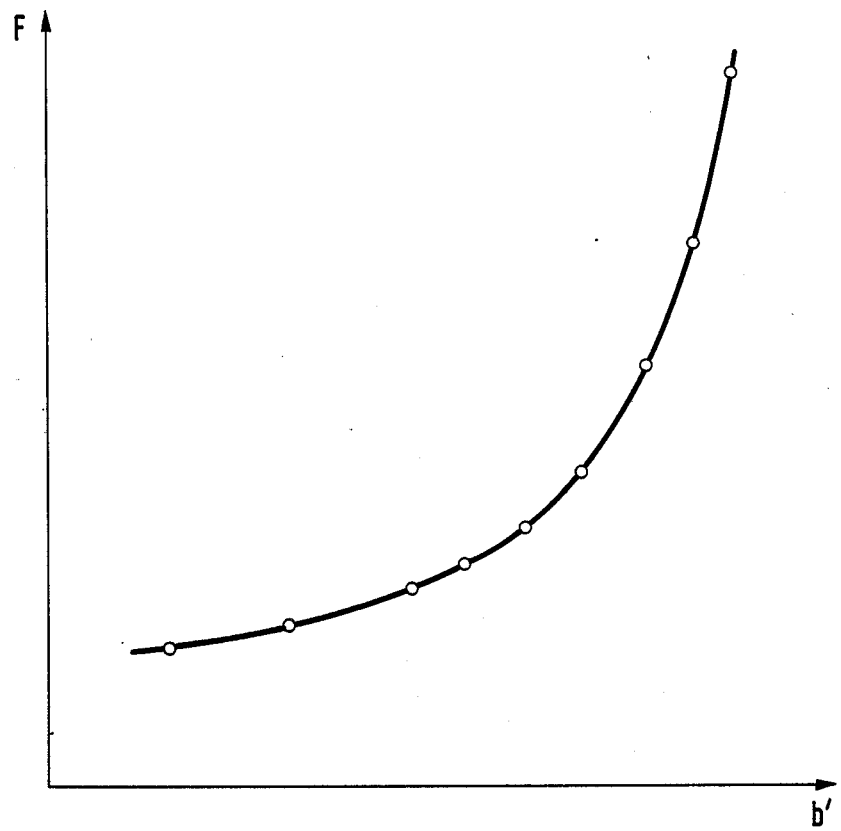
Figure 8:
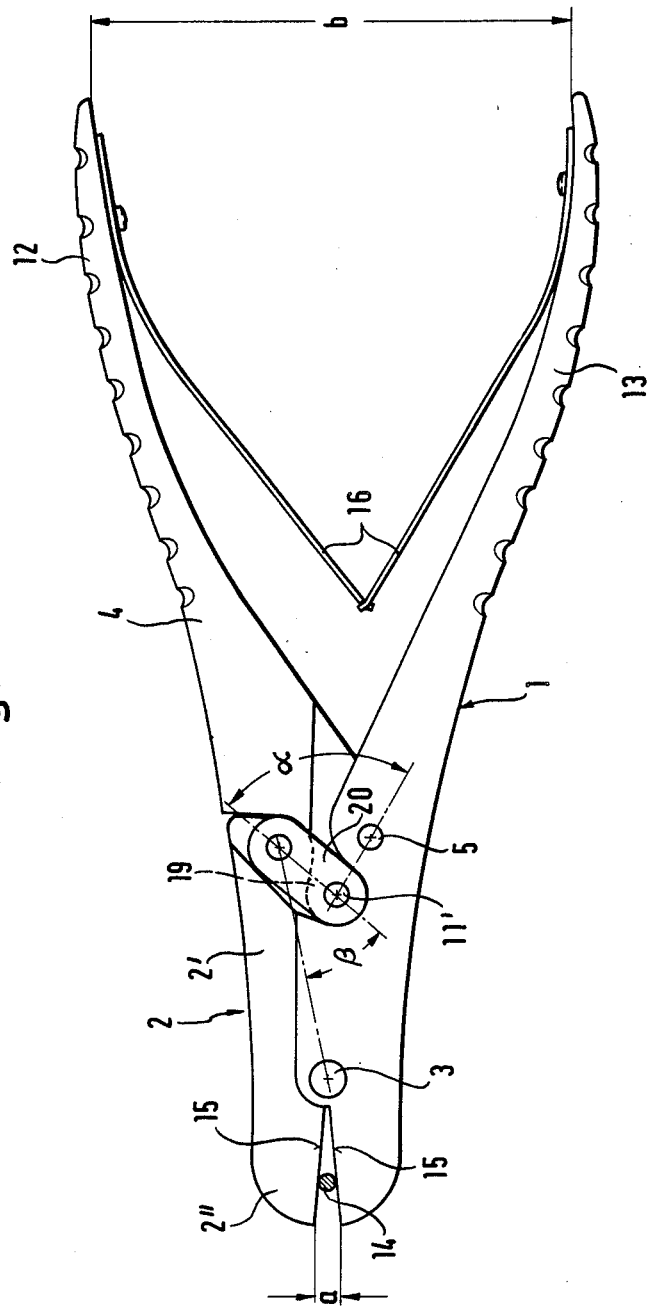

The invention will now be described by way of example only in the following and with reference to the drawings in which are shown:

FIG. 1 a plan view of a pair of surgical pliers in the opened state,

FIG. 2 a plan view of the surgical pliers of FIG. 1 in the closed state, with one part having been broken away, FIG. 3 an enlarged schematic representation of the cutting edges of a pair of surgical pliers on cutting through a wire, FIG. 4 a section essentially on the line IV—IV in FIG. 3, FIG. 5 a representation of the cutting edges with a pair of surgical pliers in accordance with FIG. 3 with the cutting edges being closed further, FIG. 6 a section essentially on the line VI—VI in FIG. 5, FIG. 7 a representation of the mechanical advantage of the pliers in dependence on their closing path, FIG. 8 a sideview of a particularly simply constructed embodiment of a pair of surgical pliers in accordance with the invention in the open state, and FIG. 9 a corresponding sideview to that of FIG. 8, however with the pliers being shown in the pressed together state.

In the various figures of the drawings parts which correspond to one another are designated with the same reference numerals.

In accordance with FIGS. 1 and 2 the surgical pliers have a cutting gripping lever 1 on which there is provided a first cutting edge 15 at the front end, i.e. the left hand end in the drawing, and a handle 13 at its rear end. A cutting lever 2 is pivotally mounted on the cutting gripping lever 1 via a cutting lever hinge 3. At its front portion the cutting lever 2 has a second cutting edge 15′ which cooperates with the first cutting edge 15, with the two cutting edges 15, 15′ being arranged in the manner of a side cutter.

Behind the cutting lever hinge 3, i.e. at the side of the cutting lever hinge 3 remote from the cutting edges 15, 15′, a gripping lever 4 is pivotally connected to the cutter gripping lever 1 via a gripping lever hinge 5 and has a handle 12 at its end remote from the gripping lever hinge 5. A transmission lever 6 is mounted via a further hinge 7 in the region of the handle 12. The transmission lever forms together with the gripping lever 4 a first toggle lever 4, 6 and acts at its other end on a toggle lever hinge 11′ of a second toggle lever 8, 10 which is formed by a support lever 8 and an intermediate lever 10.

The support lever 8 is pivotally connected via a support hinge 9 to the cutter gripping lever 1 with the support hinge being located approximately in the middle between the cutting lever hinge 3 and the handle 13 of the cutter gripping lever 1. The intermediate lever 10 pivotally connected to the toggle lever joint 11′ can be resiliently compressed and extends from the toggle lever hinge 11′ forwardly where it is connected at its front end via an intermediate hinge 11 with the rear end of the cutting lever 2.

The intermediate piece is generally of U-shape with the spring slot 18 provided between the two spring limbs 17, 17′ of the U extending substantially perpendicular to the connection line between the intermediate hinge 11 and the toggle lever hinge 11′.

The first toggle lever has an acute angle between the gripping lever 4 and the transmission lever 6 which becomes smaller on pressing the handles 12, 13 together. During this the front end of the transmission lever 6 is pressed forwardly, i.e. the direction towards the cutting edges 15, 15′ and thereby brings about a displacement of the toggle lever hinge 11′ whereby and obtuse angle of the second toggle lever 8, 10 provided between the support lever 8 and the intermediate lever 10 becomes larger.

In order to bring the pliers automatically back into their opened position a spreading spring 16 is provided between the gripping lever 4 and the transmission lever 6 which presses the transmission lever 6 away from the gripping lever 4.

The function of the surgical pliers described above will now be explained in more detail in the following with reference to FIGS. 3 to 6:

In order to cut through a wire 16, a screw or the like with the surgical pliers as described, a wire 14 is arranged in the customary manner between the cutting edges 15, 15′ and the handles 12, 13 are subsequently pressed together. During this the toggle lever hinge 11′ of the second toggle lever 8, 10 is displaced forwardly. This movement is transmitted from the resilient intermediate lever 10 via the intermediate hinge 11 to the cutting lever 2 which is then pivoted in the counter-clockwise sense relative to the cutter gripping lever 1 about the cutting lever hinge 3 so that the two cutting edges 15, 15′ move closer together and thereby penetrate into the wire to be separated, as illustrated in FIGS. 3 to 6.

During this movement the cutting edges 15, 15′ penetrate in the initial phase of the separating procedure into the round wire, which is for example shown round in the drawing, from both sides, first of all with a low contact area as can be seen from the FIGS. 3 and 4. In view of the initially small contact area of the cutting edge 15, 15′ the pressure in this phase is very high so that the generation of the pressure does not cause any difficulties.

On further penetration of the cutting edges 15, 15′ into the wire 14 the contact surface of the cutting edges 15, 15′ increases so that, as long as the cutting edges 15, 15′ are pressed together with constant force, the pressure exerted by the cutting edges 15, 15′ on the wire 14 reduces. In this way the pressure exerted by the cutting edges 15, 15′ beyond a certain depth of penetration, which depends amongst other things on the diameter of the wire 4 to be separated, becomes so small that it is no longer sufficient for the further separation of the wire 14.

In order to now keep the pressure so large that a further separation of the wire 14 is always possible, the force acting on the cutting edges 15, 15′ must likewise be increased in accordance with the increase of the contact areas of the cutting edges 15, 15′.

The FIGS. 5 and 6 now show the cutting edges 15, 15′ which have penetrated further into the wire 14 and the enlargement of the contact surfaces of the cutting edges can be clearly seen from FIG. 6.

It can now be seen that the force required for complete separation of round bodies, for example the wire 14, must increase approximately quadratically in dependence on the depth of penetration of the cutting edges 15, 15′ in order to always obtain the required separating pressure of the cutting edges 15, 15′ as the cutting process proceeds.

With the pliers as described the closing angle formed by the gripping lever 4 and the cutter gripping lever 1 becomes smaller during a cutting step. At the same time the angle of the first toggle lever 4, 6 between the gripping lever 4 and the transmission lever 6 becomes smaller until the transmission lever 6 lies always parallel to the gripping lever 4 when the pliers are closed. On the other hand, the angle of the second toggle lever 8, 10 becomes larger so that when the pliers are closed the second toggle lever 8, 10 almost adopts its extended position and the support lever 8 lies almost in line with the intermediate lever 10.

As a result the forward movement of the transmission lever 6 or of the toggle lever 11' becomes always smaller in relation to the closing movement of the handles 12, 13. The pivotal movement of the cutting lever 2 accordingly also becomes always smaller as the closing angle between the angles 12, 13 becomes smaller so that as the distance between the handles 12, 13 becomes smaller the changes of the distance a between the cutting edges 15, 15' also always becomes smaller for the same changes of the distance b. Thus the mechanical advantage (transmission ratio) for the forces acting on the handles 12, 13 becomes larger, so that the force acting on the cutting edges 15, 15' is made larger without an increase of the force on the handles 12, 13 being necessary.

In FIG. 7 the force F now exerted onto the cutting edge 15, 15' is shown for a substantially constant force acting on the handles 12, 13 of the pliers in dependence on the path b' which the handle 12 moves through relative to the handle 13 as the distance b between the handles 12, 13 becomes smaller. As the distance b between the handles 12, 13 becomes smaller, i.e. as the path b' becomes larger the force acting on the cutting edges increases whereby the increase in force corresponds to the increase of the contact surface of the cutting edges 15, 15' on the wire 14. Thus the cutting edges always exert on the wire 14 the force required to separate the wire 14.

If wires or screws of larger diameter are to be separated with the pliers as described then an increase of the force acting on the cutting edges 15, 15' is already necessary when the closing angle between the cutter gripping lever 1 and the gripping lever 4 and thus the distance b between the handles 12, 13 is still large and the automatic increase of the mechanical advantage has practically not yet occurred.

In this case the front end of the transmission lever 6, and thus the toggle lever hinge 11' of the second toggle lever 8, 10, is displaced forwardly on pressing the handles 12, 13 toqether, without the intermediate hinge 11 of the intermediate lever 10 following this movement. The intermediate hinge 11 does not follow this movement because the spring slot 18 of the resilient intermediate lever 10 is first pressed together against the spring forces exerted by the latter. As a consequence the distance a between the cutting edges 15, 15' does not initially change. As soon as the spring slot 18 in the intermediate lever 10 is closed the further displacement of the toggle lever hinge 11' brings about a displacement of the intermediate hinge 11 in dependence on the reduction of the spacing b between the handles 12, 13, thus resulting in closing of the cutting edges 15, 15'. In this region an increased mechanical advantage is now present so that the automatic increase in force comes fully into effect and the pressure exerted by the cutting edges 15, 15' onto the wire and onto the screw is now at least as large as or larger than the required separating pressure. At the same time it is made possible for the spacing between the handles 12, 13 to be reduced further than would be the case if a rigid intermediate lever were used, so that an additional increase in force required for an increase in pressure is made possible.

The embodiment of FIGS. 8 and 9 is distinguished from the preceding embodiment first of all in the fact that the spacing between the cutting lever hinge 3 and the gripping lever hinge 5 is made substantially larger. Moreover, the gripping lever 4 is also extended on the far side of the gripping lever hinge 5 in the direction of the cutting lever hinge 3 via a relatively short toggle lever arm 19 to which a toggle lever link 20 is pivotally connected via a toggle lever hinge 11', with the other end of the toggle lever link being pivotally connected with the rear arm 2' of the cutting lever 2.

In this manner a toggle lever transmission comprising the toggle lever 19, 20 is inserted between the gripping lever 4 and the cutting lever 2, with the kink angle $\alpha$ of the toggle lever 19, 20 being somewhat smaller than 90° in the open position of the pliers in accordance with FIG. 8 whereas it lies at around 135° in the pressed together position of FIG. 9.

As a result of this construction a comparatively small force is exerted on the clamped wire 14 at the start of the clamping movement of the pliers in accordance with FIG. 8. With increasing extension of the toggle lever 19, 20 the mechanical advantage however increases substantially quadratically so that a considerably enlarged cutting force is available when the wire is to be cut through at its broadest position in the sideview of FIG. 8. For this purpose it is also important that the angle $\beta$ between the lever arm 2 and the toggle lever link 20, which amounts to ca. 35° in accordance with FIG. 8, increases up to approximately 60° (FIG. 9).

The resetting force for the pliers is achieved by the double leaf spring 16 which can be seen from FIGS. 8 and 9. The double leaf spring 16 consists of two spring leaves which extend from the free end of the handles 12 and 13 in the direction of the hinge 5, with the ends of the spring leaves adjacent the hinge 5 being hingedly connected together.

The axes of all the hinges present in the pliers of the invention, in particular the cutting lever hinge 3, the gripping lever hinge 5 and also the various toggle lever hinges are perpendicular to the plane defined by the cutter gripping lever 1 and the cutting lever 2.

I claim:

1. Pliers usable for surgical purposes for cutting through wires, screws and the like, comprising:
    a cutter gripping lever having a first cutting edge at its front end, a handle at its rear end;
    a cutting lever having a second cutting edge disposed opposite to the first cutting edge;
    a cutting lever hinge pivotally connecting said second cutting edge to said cutter gripping lever;
    a gripping lever pivotally connected to the cutter gripping lever behind the cutting lever hinge by a gripping lever hinge;
    a transmission means between the gripping lever and the cutting lever hinge, said transmission means including a toggle lever drive and having an input drive member and an output drive member;
    the input drive member including a transmission lever pivotally connected at its first end to said gripping lever;
    said transmission lever and said gripping lever forming a first toggle lever;
    the other end of the transmission lever loading a toggle lever hinge of a second toggle lever, said second toggle lever including a support lever pivotally connected to said cutter gripping lever and an intermediate lever, said intermediate lever extending from said toggle lever hinge to said cutting lever, said intermediate lever pivotally connected at an intermediate hinge;

wherein said input drive member of the transmission means is loaded by said gripping lever and said output drive member of the transmission means acts on said cutting lever at the side remove from the cutting edge of the cutter lever hinge which supports the cutting lever on the cutter gripper lever; and wherein like relative pivotal movements of said gripping lever relative to said cutter gripping lever bringing about progressively smaller pivotal movements of said cutting lever relative to said cutter gripping lever as the distance between said cutting lever and said cutter gripper lever becomes smaller, so that the mechanical advantage increases automatically as the distance becomes smaller.

2. Pliers in accordance with claim 1, characterised in that the mechanical advantages increases substantially quadratically as the distance (b) between the gripping lever (4) and the cutter gripping lever (1) becomes smaller.

3. Pliers in accordance with claim 1, characterised in that an acute angle which becomes smaller on actuating the pliers is provided between the gripping lever (4) and the transmission lever (6), and in that an obtuse angle which becomes larger on actuating the pliers is provided between the support lever (8) and the intermediate lever (10), wherein, when the cutting edges (15, 15') are closed, the transmission lever (6) lies approximately parallel to the gripping lever (4) and the second toggle lever (8, 10) lies shortly before its extended position.

4. Pliers in accordance with claim 1, characterised in that the length of the intermediate lever (10) can be reduced.

5. Pliers in accordance with claim 4, characterised in that the intermediate lever (10) is formed as a spring.

6. Pliers in accordance with claim 5, characterised in that the intermediate lever (10) is formed by a U-shaped compression spring, the spring slot (18) of which brings about the change in length of the intermediate lever (10).

7. Pliers in accordance with claim 1, characterised in that the gripping lever (4) is extended on the far side of the gripping lever hinge (5) by a relatively short toggle lever arm (19) which, via a toggle lever hinge (11'), acts on a toggle lever link (20) which together with the toggle lever arm (19) forms a toggle lever (19, 20) and which is pivotally connected at the end remote from the toggle lever joint (11') to the lever arm (2') of the cutting lever (2) remote from the cutting edge (15) with respect to the cutting lever hinge (3), with the toggle lever (19, 20) passing on reduction of the spacing (b) between the gripping lever (4) and the handle (13) from a greatly kinked position into a more extended position, and with the toggle lever link (20) including a substantial angle of preferably at least 30° to 40°, in particular 35° with the said lever arm (2') in the opened state of the pliers, with this angle expediently progressively approaching 90° as the cutting edges 15, 15' move together and/or preferably amounting to 40° to 80°, expediently to 60° to 70° and in particular to approximately 60°, when the cutting edges (15, 15') are closed or are approximately closed.

8. Pliers in accordance with claim 7, characterised in that the toggle lever (19, 20) has a kink angle α of the order of magnitude of 90° and preferably somewhat less than 90°, in particular approximately 80° to 90°, in the non-actuated state of the pliers and, in the fully compressed state of the pliers is located close to its extended state and preferably has a kink angle α between 120° and 150°, preferably 130° to 140°.

9. Pliers in accordance with claim 7, characterised in that the lever arm (2') between the cutting lever hinge (3) and the toggle lever link (20) is longer by a factor 1.5 to 2 than the lever arm (2") carrying the cutting edge (15').

10. Pliers usable for surgical purposes for cutting through wires, screws and the like, comprising:

a cutter gripping lever having a first cutting edge at its front end, a handle at its rear end;

a cutting lever having a second cutting edge disposed opposite to the first cutting edge;

a cutting lever hinge pivotally connecting said second cutting edge to said cutter gripping lever;

a gripping lever pivotally connected to the cutter gripping lever behind the cutting lever hinge by a gripping lever hinge;

wherein said gripping lever extends on the far side of the gripping lever hinge by a relatively short toggle lever arm, said toggle lever arm acting on a toggle lever link via a toggle lever hinge, said toggle lever link together with said toggle lever arms forms a toggle lever hinge to a lever arm of said cutting lever remote from the cutting edge with respect to the cutting lever hinge;

wherein said toggle lever passing on reduction of the spacing between said gripping lever and said handle from a greatly kinked position into a more extended position, said toggle lever link including a substantial angle with said lever arm in the opened state of the pliers, with said angle expediently progressively increasing as the cutting edges move together when the cutting edges are closed or are approximately closed;

a transmission means between the gripping lever and the cutting lever hinge, said transmission means having an input drive member and an output drive member;

wherein said input drive member of the transmission means is loaded by said gripping lever and said output drive member of the transmission means acts on said cutting lever at the side remote from the cutting edge of the cutting lever hinge which supports the cutting lever on the cutter gripper lever; and wherein like relative pivotal movements of said gripping lever relative to said cutting gripping lever bringing about progressively smaller pivotal movements of said cutting lever relative to said cutter gripping lever as the distance between said cutting lever and said cutter gripping lever becomes smaller, so that the mechanical advantage increases automatically as the distance becomes smaller.

11. Pliers in accordance with claim 10 wherein said angle between said gripping lever and said handle of preferably at least 30° to 40°, in particular 35°, said angle expediently progressively approaching 90° as said cutting edges move together, preferably mounting to 40° to 80°, expediently to 60° to 70° and in particular to approximately 60°.

* * * * *